Figure 1:
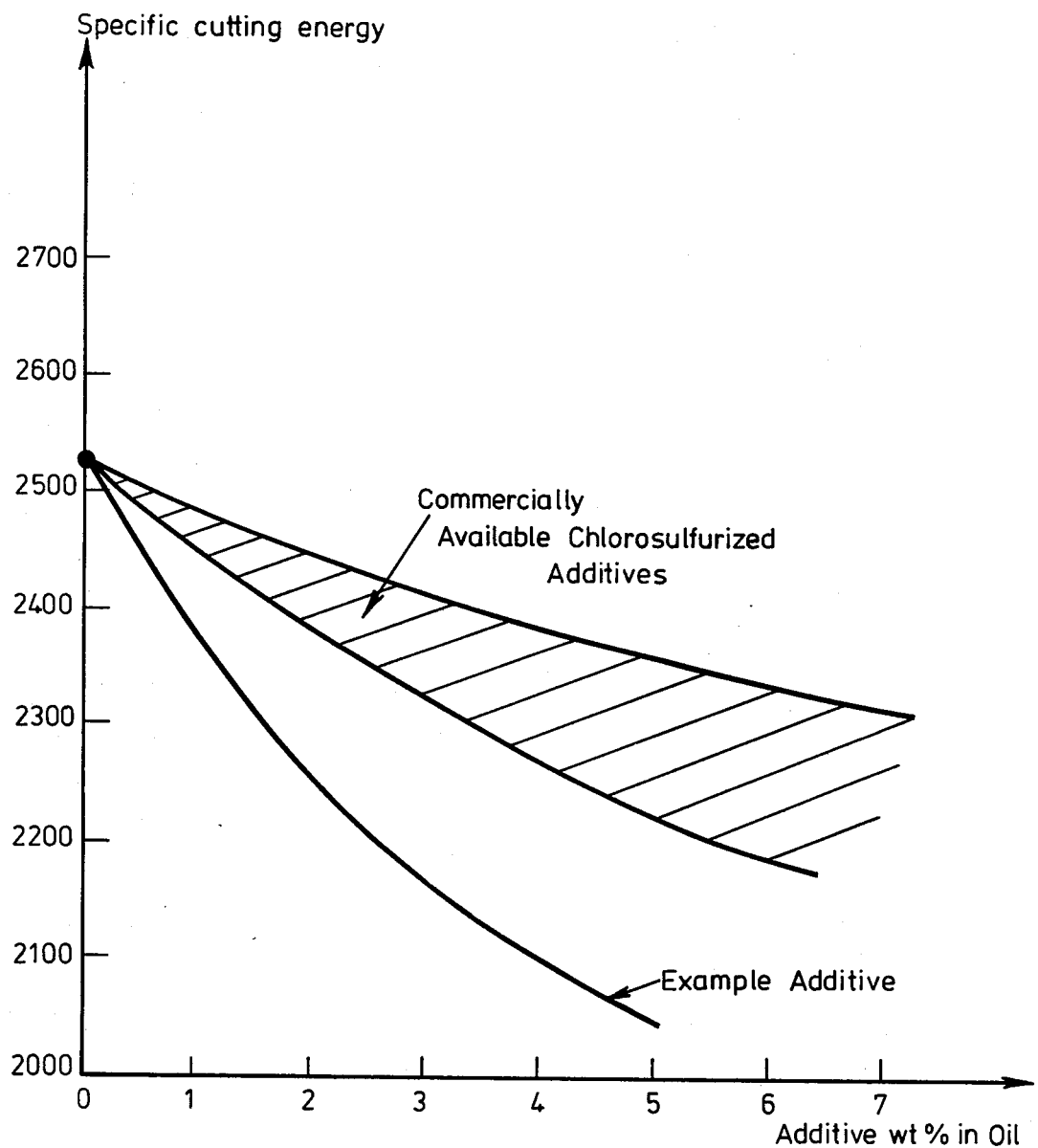

United States Patent [19]

Lenack

[11] 4,228,021
[45] Oct. 14, 1980

[54] CHLORO-SULPHUR ADDITIVE

[75] Inventor: Alain L. P. Lenack, Mont-Saint-Aignan, France

[73] Assignee: Exxon Research & Engineering Co., Florham Park, N.J.

[21] Appl. No.: 1,411

[22] Filed: Jan. 8, 1979

Related U.S. Application Data

[63] Continuation of Ser. No. 801,027, May 27, 1977, abandoned, which is a continuation-in-part of Ser. No. 639,865, Dec. 11, 1975, abandoned.

[30] Foreign Application Priority Data

Dec. 17, 1974 [GB] United Kingdom ............... 54398/74

[51] Int. Cl.$^2$ ..................... C10M 1/46; C10M 1/38
[52] U.S. Cl. ............... 252/32.7 R; 252/33.4; 252/42.7; 252/48.8
[58] Field of Search ............... 252/33.4, 42.7, 48.8, 252/32.7 R

[56] References Cited

U.S. PATENT DOCUMENTS

| | | | |
|---|---|---|---|
| 2,247,046 | 6/1941 | Berger et al. ................ | 252/48.8 |
| 2,296,037 | 9/1942 | Kaufman ...................... | 252/48.8 X |
| 2,514,625 | 7/1950 | Clausen et al. .............. | 252/48.8 X |
| 2,560,421 | 7/1951 | Eby ............................... | 252/48.8 X |

OTHER PUBLICATIONS

Rabe et al., CA 66:77996z (1967).

*Primary Examiner*—Thomas A. Waltz
*Attorney, Agent, or Firm*—Frank T. Johmann

[57] ABSTRACT

Compounds suitable as extreme pressure additives for lubricating oils are of the general formula $$CX_3\text{-S-S-R}$$

where X is a halogen and R is a hydrocarbyl. The performance of the compounds is improved by the addition of a stabilizer.

17 Claims, 2 Drawing Figures

CHLORO-SULPHUR ADDITIVE

This is a continuation of application Ser. No. 801,027, filed May 27, 1977 which was a continuation-in-part application of Ser. No. 639,865 filed Dec. 11, 1975, and both now abandoned.

The invention relates to lubricating products. It is concerned with halogenated sulphur compounds which, when used as additives in a lubricating composition, confer "extreme pressure" properties on the latter.

Three conventional lubricating systems are distinguished, according to the conditions under which the parts concerned rub against one another. In hydrodynamic systems, a film of liquid separates the two adjacent surfaces by circulating between them; the viscosity of the lubricant is a preponderant factor of this system of lubrication. In limiting or oily systems, lubrication is ensured by the absorption of the lubricant on the surfaces engaged in friction; the latter are separated only by very thin layers of absorbed molecules. Without being limited to such the present invention is concerned more especially with a third lubricating system, the "extreme pressure" system.

In certain instances, two pieces of steel ruo under so heavy a load that no liquid is able to form a continuous protective film between the surfaces in contact. This type of friction occurs in particular in wire drawing and metal-cutting; it also takes place in certain gears. In such cases, recourse must be had to lubricants containing special additives, termed "extreme pressure". These are organic compounds which liberate phosphorus, sulphur or chlorine when they are heated to a high temperature. These metalloids are liberated and combine with iron through the effect of local heating which causes dry friction between the surfaces in contact. The steel parts are thus protected by a thin layer of phosphide, sulphide or chloride and can endure friction under much heavier loads without welding or seizing.

The lubricating products of our invention are particularly useful as metal working lubricants. The importance of extreme pressure additives in metal working depends upon the type of work to which the metal is subjected. Generally the more severe the cutting technique the lower the cutting speed and the greater the importance of extreme pressure additives. Thus, whilst certain additives are useful in high speed cutting operations they are not sufficiently effective to be used in the more severe lower speed operations.

The usual extreme-pressure additives are phosphoric esters, chlorinated paraffins, sulphurised fats, dithiocarbamates, xanthates, organic sulphides etc. A mixture of chlorinated paraffins and sulphurised sperm oil is very often used. Generally the sulphochlorinated additives are the most effective in the low speed, most severe cutting operations. However, one problem with the use of sulphochlorinated additives is that hydrochloric acid tends to be liberated during cutting which is corrosive.

It has been proposed in U.S. Pat. Nos. 2,247,042, 2,247,043; 2,247.044; 2,247,045 and 2,247,046 to use various reaction products of perchloromethylmercaptan as extreme pressure additives. For example U.S. Pat. No. 2,247,046 describes using the compound obtained by reacting perchloromethyl mercaptan with compounds of the general formula RSX where R may be alkyl, aryl, aralkyl or alkaryl, examples being given of compounds where R is alkyl containing up to 6 carbon atoms.

Some of these products have a disulphide group linked directly to R and we have found that where this linkage is directly to an aromatic nucleus the extreme pressure properties of the compounds are reduced. We have also found that the compounds described in U.S. Pat. No. 2,247,046 cannot conveniently be used as extreme pressure additives because the mercaptans from which they are made tend to be too volatile and evaporate at the reaction temperatures and they have low flash points. Furthermore the use of these compounds can lead to corrosion since they liberate hydrochloric acid in use.

My invention is therefore concerned with highly potent sulphohalogenated extreme pressure additives which are effective in the low speed severe cutting operations and which are less prone to liberate corrosive acids during use.

My invention therefore provides compounds of the chemical formula $XY_2C-S-S-R$, in which:

R represents a monovalent hydrocarbon radical containing from 8 to 30 carbon atoms.

X represents a halogen atom, or a monovalent hydrocarbon radical in which one or more hydrogen atoms are substituted by halogen atoms, and Y represents a halogen atom.

R may be an alkyl, aromatic or alkyl aromatic radical. It is for preference that the disulphide group is linked to an alkyl carbon atom and we prefer then R is an alkyl radical, normal or branched, containing 8 to 30 preferably 8 to 18 carbon atoms.

X is for preference a halogen atom and the formula of the compound is written $Y_3C-S-S-R$.

In all cases the preferred halogen atom is chlorine and the preferred compound has the formula $Cl_3-C-S-S-R$.

These compounds are soluble in oil and we have also found that in the compounds of our invention which contain the $S-S-CXY_2$ structure with the carbon atom bonded to both sulphur and halogen the carbon/sulphur bond is considerably weaker than in compounds which contain the $S-S-C-C$-halogen structure such as those of U.S. Pat. No. 2,560,241. This in turn leads to more ready liberation of sulphur and improved extreme pressure properties. We also find that the halogen atoms of the preferred compounds of our invention make a greater contribution to extreme pressure properties when part of a trihalo methyl group.

One problem in using this type of compound is that any residual hydrochloric acid in the compound tends to decompose the additive as do acids evolved due to the higher temperatures generated in metal working but we have found that this may be overcome by incorporating a stabilizer in the additive composition. The present invention is therefore also concerned with compositions containing these new halo-sulphur compounds together with a stabilizer which minimises the problem caused by the presence of hydrochloric acid, the invention is also concerned with the use of these compositions as lubricant additives.

The present invention therefore provides a composition comprising an oil containing (i) a compound of the chemical formula XY$_2$C—S—S—R in which R represents a monovalent hydrocarbon radical containing from 4 to 30 carbon atoms X represents a halogen atom or a monovalent hydrocarbon radical in which one or more hydrogen atoms are substituted by halogen atoms and Y represents a halogen atom and (ii) a stabiliser which acts as an acid trap and inhibits liberation of halogen and sulphur at temperatures below 200° C.

R may be an alkyl, aromatic or alkyl aromatic radical and it is preferred that the disulphide is linked to an alkyl carbon atom. With R containing from 8 to 30 atoms the combined benefits of improved oil solubility and lower volatility are coupled with the improved properties imparted by the stabiliser.

In including the stabiliser in the composition of the present invention the stability of an extreme-pressure additive composition is enhanced at temperatures up to 200° C. and the liberation of chlorine and sulphur at lower temperatures is inhibited. The stabiliser makes little if any contribution to the extreme-pressure properties of the additive but acts as an acid trap and thus prevents corrosion and premature liberation of halogen and sulphur up to 175° C., preferably up to 200° C. and any compound that achieves this effect may be used. The prime function of the stabiliser is thus not to remove corrosive materials from the product to be used as an extreme pressure additive but to inhibit formation of undesirable corrosive products during use and to remove any that may be formed.

The stabilisers that may be used in this composition should be soluble in oil and are generally basic. Basic alkaline earth metal alkylbenzene sulphonates and basic alkaline earth metal alkyl phenates are particularly suitable. For example high base number calcium or magnesium sulphonates or phenates are preferred. Alternatively an epoxy resin may be used. The formulation should generally contain from 0.5 to 5% by weight of the stabiliser in relation to the halo-sulphur compound to impart the desired stability at temperatures less than 200° C. Other examples of suitable stabilisers include dicarboxylic acid esters, salts of fatty acids (such as the calcium salt of tall oil fatty acid) and heterocyclic nitrogen containing compounds such as thiadiazoles. Blends of two or more of these materials may be used. The stabiliser may conveniently be added to the chlorosulphur compound after the latter has been purified.

We prefer to use high base number calcium or magnesium sulphonate since sufficient stability may generally be achieved with a smaller quantity of stabiliser which is of advantage since the additives are generally supplied as concentrates in oil containing up to 60% by weight of the sulphochlorinated compound and the stabiliser and the concentrate may not be able to hold larger quantities, for example more than 3% and in some instances more than 2% by weight of stabiliser based on the chlorosulphur compound.

It is also desirable to add an anti-corrosion compound to the composition containing the compound and the stabiliser.

The invention therefore provides an extreme-pressure additive composition characterised in that it comprises:

A. The halo-sulphur compound of the general formula XY$_2$C—S—S—R in which

R represents a monovalent hydrocarbon radical containing from 4 to 30 carbon atoms.

X represents a halogen atom or a monovalent hydrocarbon radical in which one or more hydrogen atoms are substituted by halogen atoms and Y represents a halogen atom B. a thermal stabiliser soluble in hydrocarbon oils C. an anti-corrosion agent soluble in hydrocarbon oils.

As with the formulation of the present invention R may be an alkyl, aromatic or alkyl aromatic radical and it is preferred that the disulphide is linked to an alkyl carbon atom. It is also preferred that R contains from 8 to 30 carbon atoms to achieve the benefits of improved oil solubility and lower volatility.

Any anti-corrosion or antirust agent that is soluble in hydrocarbon oils may be used and we prefer to use a barium or calcium salt of a carboxylic acid.

Alternatively we may use a sodium alkylbenzene sulphonate of high molecular weight, etc. We prefer to use from 0.5 to 10% by weight of the anti-corrosion agent and our preferred anti-corrosion agent is barium dinonyl sulphonate and we find that composition containing 0.5 to 10% barium dinonyl sulphonate in relation to the halo-sulphur compound is not corrosive to steel or copper.

The composition of the present invention may be a liquid or semi-liquid lubricating composition, and preferably contains a minor proportion by weight e.g. from 0.1 to 10% or for preference from 0.2 to 5% by weight of halo-sulphur compound, and the preferred amounts of the stabiliser and anti-corrosion agent described above.

The compound according to the invention owes its extreme-pressure lubricating power to the fact that is decomposes liberating halogen and sulphur through the action of heat. It is desirable for the latter to be produced only in contact with the steel that is locally heated by dry friction to temperatures above about 200° C.

For a liquid lubricant the additives are merely dissolved in a suitable base oil which may be a refined mineral oil having a viscosity from 10 to 300 cS to 50° C. or a synthetic oil. Where the composition is semi-liquid it may be a lubricating grease which then contains a base oil and suitable thickeners such as fatty acid soaps.

The formulation of the present invention may be used in lubricants in cutting oils emulsified in water by means of a suitable emulsifier. Any conventional emulsifier may be used although we prefer to use emulsifiers based on alkylaryl sulphonates particularly sodium alkylaryl sulphonates. Our preferred emulsifier systems are those comprising mixtures of alkylaryl sulphonates having two distinct molecular weight maxima as are described in our French patent applications Nos. 7408003 and 7424875.

The chloro-sulphur compounds and the composition and formulation of the present invention are conveniently supplied as concentrates of the compounds in oil. The invention is also concerned with concentrates comprising mineral oil containing from 10% to 60% by weight of the concentrates of the compound, composition or formulation of the present invention. This concentrate may also contain the emulsifier.

In yet a further aspect the present invention relates to a process for making the new halo-sulphur compounds.

The process is characterised in that it comprises the reaction:

of a perhalomercaptan, whose chemical formula is $XY_3—C—SY$ in which X represents a halogen atom (preferably chlorine) or a monovalent hydrocarbon radical, in which one or more hydrogen atoms are substituted by halogen atoms, and Y is a halogen atom, preferably chlorine
and a thioalcohol, a thiophenol or an alkyl thiophenol, whose chemical formula is: HS—R
in which R represents a monovalent hydrocarbon radical having 8 to 30 carbon atoms, the said reaction being written thus:

$$XY_2C—SY + HSR \rightarrow XY_2C—S—S—R + HY$$

For preference, the perchloromercaptan is perchloromethylmercaptan and the reaction is written:

$$Cl_3C—SCl + HS—R \rightarrow Cl_3C—S—S—R + HCl$$

The perhalomercaptan, for preference perchloromethylmercaptan, is reacted with a thioalcohol, a thiophenol, or an alkylthiophenol.

It is possible to use a mono or dialkylthiophenol whose alkyl groups may contain up to 24 carbon atoms. For instance, it is possible to use a dodecylthiophenol manufactured by means that are known per se from the alkylation product of benzene with tetrapropylene.

Ahy thioalcohol with normal or branched chain whose molecule contains from 8 to 18 carbon atoms may be used. Use is made for preference of a branched chain thioalcohol prepared by means that are known per se, from a propylene oligomer. The branched-chain thioalcohol that is regularly prepared from technical tetrapropylene is particularly useful in the process.

It is sufficient merely to bring the two reagents into contact. The reaction takes place spontaneously at the ordinary temperature, at 15° C. for example. It is exothermic, and cooling is therefore essential. The yield is high and can be 100%.

The reaction is performed in a reactor that is not attacked by a hydrohalic acid e.g. hydrochloric acid, for instance borax glass equipment. The reactor is provided with means for eliminating the heat of the reaction and with means for recovering the hydrogen halide gas that is liberated.

In order to prevent the reaction from getting out of hand, the operation is preferably effected as follows: All of one of the reagents, is placed in the reactor and the other gradually added at a rate where the generation of heat and hydrogen halide gas are under control. The reaction can be performed over a wide temperature range. A temperature of 20° to 50° C. is perfectly suitable. It is possible to operate at a higher temperature, for instance at a temperature of 50° to 100° C., if the reactor is provided with an effective rising refrigerant.

The present invention is illustrated but in no way limited by reference to the following examples.

EXAMPLE 1

In a glass three necked 1 liter flask, cooled on the outside by an ice bath and fitted with a thermometer, a bromine phial and a gas discharge tube, were placed 202 g (1 mole) of "tertiododecylmercaptan" ("tertiododecylmercaptan" is the common name of the mercaptan derived from technical tetrapropylene).

There were then placed gradually in the flask, through the bromine phial, 186 g (1 mol.) perchloromethylmercaptan. The perchloromethyl mercaptan was introduced in 1 hour, the flask being cooled. In this way the temperature was kept between 20° and 30° C. Half an hour after the end of the introduction of perchloromethylmercaptan, the liberation of hydrochloric acid had ceased. The flask then contained 351 g (1 mole) of the product of the reaction:

$$Cl_3C—SCl + HS—C_{12}H_{25} \rightarrow Cl_3C—S—S—C_{12}H_{25} + HCl$$

The product obtained distil between 110° and 115° C. under 0.1 mm mercury. Its refractive index (nD20° C.) is 1.5235.

The chlorine and sulphur in this product were determined. The contents found differ very little from the calculated contents

|  | Found | Calculated |
|---|---|---|
| Chlorine (% by weight) | 30.2 | 30.5 |
| Sulphur (% by weight) | 18.0 | 18.3 |

A composition (M) of additive for extreme-pressure lubricant was prepared by mixing:
95% by weight of chlorosulphur product
2% by weight of epoxy resin, and
3% by weight of barium dinonylsulphonate.

The epoxy resin was the commercial product that is sold under the trade name of EPIKOTE 812.

There were then prepared according to the invention two extreme-pressure lubricants A and B, by dissolving respectively 3.3 and 0.5% by weight of the composition M in a refined mineral oil having a viscosity of 33 cSt at 37.8° C.

By way of comparison an extreme-pressure lubricant (C) of a known type was prepared by dissolving in the said base oil 5% by weight of sulphurised sperm oil and 1.4% by weight of chlorinated paraffin (containing 70% chlorine).

These lubricants were tested by means of the 4-ball extreme-pressure machine, according to the American standard ASTM D 2783. The results are collated in the following table.

| Type of lubricant Reference | According to invention | | Conventional |
|---|---|---|---|
|  | A | B | C |
| Composition M (% by weight) | 3.3 | 0.5 | — |
| Chlorinated Sperm oil (by weight) | — | — | 5.0 |
| Chlorinated paraffin (by weight) | — | — | 1.4 |
| Mineral oil | 96.7 | 99.5 | 93.6 |
| Sulphur content (% by weight) | 0.6 | 0.09 | 0.6 |
| Chlorine content (% by weight) | 1.0 | 0.15 | 1.0 |
| Results of extreme pressure tests Mean load (Hertz) | 88 | 42 | 43 |
| Welding load | 800 | 316 | 251 |

Further tests on lubricant A shown even better extreme pressure properties with a mean Hertz load above 120 kilograms and welding loads above 800 kilogrammes.

It is surprising to note that lubricant A, which has the same content of sulphur and chlorine as lubricant C, has very much better extreme-pressure properties.

Lubricant B has extreme-pressure properties comparable with those of the conventional lubricant C, but with much smaller sulphur and chlorine contents.

Lubricant A is stable at 175° C. and is not corrosive in relation to either steel or copper.

To verify the stability of this lubricant, a 25 g sample is placed in a glass test tube. A moderate air supply is bubbled into the sample which is kept at 175° C. The air which has passed through the test tube is then brought into contact with a determined volume of a titrated sodium hydroxide solution. After 4 hours' test, the acid neutralised by the sodium hydroxide is back titrated.

No hydrochloric acid was detected (the test is sensitive to 0.01% by weight of HCl in relation to the weight of lubricant).

The corrosion of the steel was evaluated according to the American standard ASTM D 665 A and B, with a length of test of 24 h with no rust formation.

The corrosion of the copper was tested according to ASTM standard D 130. The result of this test is excellent (rating 1a).

Similar tests on both lubricants A and B containing no stabiliser showed similar extreme pressure properties but a significant increase in copper and steel corrosion.

EXAMPLE 2

The process of Example 1 was repeated replacing the tertiododecylmercaptan with 60 grams of tertiononyl mercaptan (the mercaptan derived from technical tripropylene).

The temperature was maintained in the range 20° to 60° C. and after stripping with nitrogen at 90° C. for 4 hours the yield was 309 grams of a product containing 33.3% by weight of chlorine and 20.9% by weight of sulphur. The theoretical contents of the compound $$Cl_3C-S-S-C_9H_{19}$$

are 34.4% by weight of chlorine and 20.7% by weight of sulphur.

A composition suitable as an extreme pressure lubricant was prepared by mixing
97% by weight of the chlorosulphur product
1% by weight of overbased calcium sulphonate
2% by weight of sodium alkylbenzene sulphonate The extreme pressure lubricants D and E were then prepared containing 3.0% and 0.45% by weight of the additive in the lubricating oil of Example 1 and the lubricants subjected to the 4-ball extreme pressure test with the following results.

| Type of lubricant | D | E |
|---|---|---|
| Sulphur content in oil | 0.6 | 0.09 |
| Chlorine content in oil | 1.0 | 0.15 |
| 4 ball test (kg) | | |
| Mean Hertz Load | 120 | 41 |
| Welding Load | 800 | 315 |

As in Example 1 the additives were found to be more corrosive when the stabiliser was omitted but had similar extreme pressure properties

EXAMPLE 3

The process of Example 1 was repeated firstly using thiophenol and also dodecylthiophenol in place of the tertiododecylmercaptan and when blended with epoxy resin and barium dinonyl sulphonate, and subjected to the extreme pressure tests and compared with the products of Examples 1 and 2, the results were as follows:

| Product | 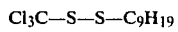—$S_2CCL_3$ | $C_{12}H_{25}$—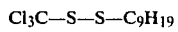—$S_2CCL_3$ | $C_{12}H_{25}-S_2-CCl_3$ | $C_9H_{19}S_2CCl_3$ |
|---|---|---|---|---|
| % Additive | 0.36 | 0.60 | 0.50 | 0.45 |
| % sulphur in lubric. | 0.09 | 0.09 | 0.09 | 0.09 |
| % chlorine | 0.15 | 0.15 | 0.15 | 0.15 |
| E.P. Performance | | | | |
| Mean Hertz load | 36 | 33 | 42 | 42 |
| Weld Load | 282 | 224 | 316 | 316 |

EXAMPLE 4

The formulations A and B of Example 1 were compared with similar formulations from which the epoxy resin/barium dinonylsulphonate stabilizer system was omitted. Similarly formulations D and E of Example 2 were compared with similar formulations from which the calcium sulphonate/sodium alkylbenzene sulphonate stabilizer system was omitted.

The extreme pressure properties were determined by the Hertz 4 ball test and the corrosive effect to copper by the ASTM D 130 Test and that to steel by the ASTM D 665 A and D 665 B tests. The test results were as follows:

| Lubricant | A | | B | | D | | E | |
|---|---|---|---|---|---|---|---|---|
| Stabiliser | Yes | No | Yes | No | Yes | No | Yes | No |
| 4 Ball Test (Kg) | | | | | | | | |
| Mean Hertz Load | 120 | 120 | 42 | 42 | 120 | 120 | 41 | 41 |
| Welding Load | 800 | 800 | 315 | 315 | 800 | 800 | 315 | 315 |
| Copper Corrosion | | | | | | | | |
| ASTM D 130 | 1a | 2a | 1a | 1b | 1a | 2a | 1a | 1b |
| Steel Corrosion | | | | | | | | |
| ASTM D 6665 A | Pass | Fail | Pass | Fail | Pass | Fail | Pass | Fail |
| ASTM D 665 B | Pass | Fail | Pass | Fail | Pass | Fail | Pass | Fail |

EXAMPLE 5

The performance of chlorosulphur product of example 1 was evaluated in a low speed cutting test in which the Specific Cutting Energy (W) is measured, this being the energy needed to separate a given volume of metal from a workpiece under standard conditions and is measured in Joules/cm³. Differences in Specific Cutting Energy lost due to friction between the cutting tool and the workpiece thus give a comparison of the efficiencies of the lubricating oils.

In practice a chip is removed from the workpiece by a two-dimensional cut into a tool whose cutting speed is maintained constant. The cutting forces are measured electrically using a piezo-quartz system and the lubricant is injected at a constant rate into the scope formed by the removal of the chip.

Various tests were carried out on a paraffinic mineral cutting oil containing different amounts of an additive package comprising 97 wt.% of a 95 wt.% active ingredient trichloromethyl tertiary dodecyl disulphide 1 wt.% of a high base number calcium alkyl benzene sulphonate as stabiliser 2 wt.% of sodium alkyl benzene sulfonate as antirust additive The performance of the cutting lubricant was compared with cutting lubricants containing similar amounts of four commercially available sulfochlorinated extreme pressure additives. The chemical compositions of these additives are not known but they were analysed for sulphur and chlorine content and two series of tests were carried out with oils of containing similar wt.% of the additives and the other with oils having similar sulphur and chlorine contents.

The performance of lubricants containing equal amounts of the additives is shown in the graphs attached hereto as FIG. 1 showing that under low speed conditions (6 meters per minute) a significant improvement in extreme pressure properties may be achieved using smaller proportions of the materials of this application.

Figure 2:
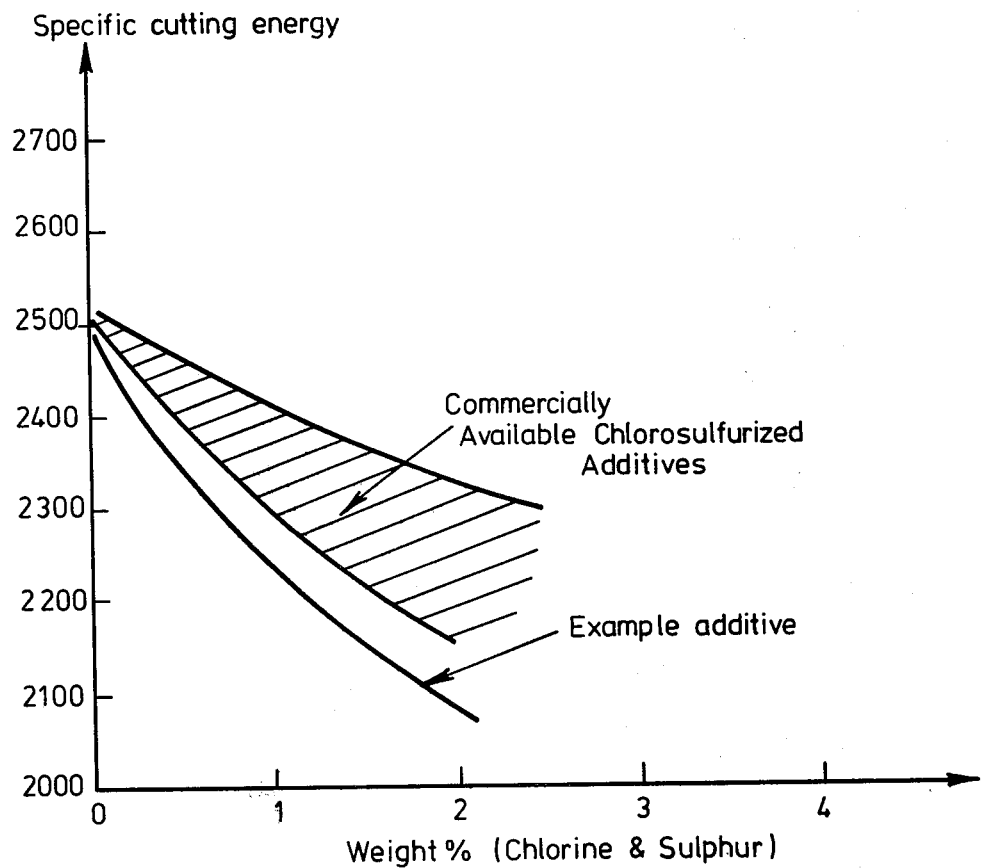

The graph of FIG. 2 gives a comparison of the material of our Example 1 with the commercially available additives in which the lubricating oils contain similar amounts of sulphur and chlorine.

EXAMPLE 6

Extreme pressure additive compositions were prepared similar to lubricant A of Example 1 but containing the following different stabiliser systems were prepared and tested.
(1) Overbased Calcium Sulphonate
(2) Overbased Barium Phenate
(3) Ester of Alkyl Succinic Acid
(4) The Thiadiazole derivative sold as Amoco 150
(5) The Calcium Salt of Tall Oil Fatty Acid
(6) Blends of the Calcium Salt of Tall Oil Fatty Acid with
  (i) Overbased Barium Phenate
  (ii) Overbased Barium Phenate
  (iii) Ester of Alkyl Succinic Acid
  (iv) Amoco 150
  (v) Epoxy resin used in Example 1

In all instances the extreme pressure and corrosion properties were substantially the same as for lubricant A of Example 1.

We claim:

1. An extreme pressure lubricating composition comprising a major proportion of lubricating oil, about 0.1 to 10 wt. % of an extreme pressure compound of the formula:

$$Cl_3C-S-S-R$$

wherein R is an alkyl radical containing 4 to 30 carbon atoms, said extreme pressure compound tending to liberate HCl; and about 0.5 to 5% by weight, based on the weight of said extreme pressure compound, of an oil soluble basic stabilizer which acts as an acid trap by reacting with said HCl and inhibits its liberation of chlorine and sulphur from said extreme pressure compound at temperatures below 200° C.

2. A composition according to claim 1, wherein R is a polypropylene group.

3. A composition according to claim 2, in which said stabilizer is a basic alkaline earth metal alkyl phenate.

4. A composition according to claim 2, in which said stabilizer is a basic alkaline earth metal sulphonate.

5. A composition according to claim 2, in which said stabilizer is an epoxy resin.

6. A composition according to claim 1, containing in addition, about 0.5 to 10% by weight, based on the weight of said extreme pressure compound, of an antirust agent which is soluble in the oil and which differs from said stabilizer.

7. A composition according to claim 6, in which the anti-rust agent is selected from the group consisting of barium or calcium salts of carboxylic acid, sodium alkylbenzene sulfonate and barium dinonyl sulfonate.

8. An extreme pressure cutting oil composition comprising a major amount of mineral lubricating oil, and 0.1 to 10 wt. % of an extreme pressure improving amount of compound of the formula:

$$Cl_3C-S-S-R$$

wherein R is an alkyl radical containing 8 to 30 carbon atoms, said compound tending to liberate HCl; and about 0.5 to about 5% by weight, based on the weight of said extreme pressure compound, of an oil soluble basic stabilizer which acts as an acid trap by reacting with said HCl and inhibits liberation of halogen and sulphur from said extreme pressure compound at temperatures below 200° C., said stabilizer being selected from the group consisting of basic alkaline earth metal alkylbenzene sulphonates, basic alkaline earth metal alkyl phenates, epoxy resins, dicarboxylic acid esters, salts of fatty acids and heterocyclic nitrogen containing compounds, and mixtures thereof.

9. A composition according to claim 8, wherein R is a branched chain alkyl group selected from the group consisting of nonyl and dodecyl radicals.

10. A composition according to claim 9, wherein R is said nonyl radical and is tripropylene.

11. A composition according to claim 9, wherein R is said dodecyl radical and is tetrapropylene.

12. A composition according to claim 8, in which said stabilizer is said basic alkaline earth metal alkyl phenate.

13. A composition according to claim 8, in which said stabilizer is said basic alkaline earth metal sulphonate.

14. A composition according to claim 8, in which said stabilizer is said epoxy resin.

15. A composition according to claim 8, which also contains about 0.5 to 10 wt. %, based on the weight of said extreme pressure compound, of an oil soluble antirust agent which differs from said stabilizer.

16. A composition according to claim 15, wherein said anti-rust agent is selected from the group consisting of barium dinonyl sulfonate and sodium alkylbenzene sulfonate.

17. A concentrate for forming an extreme pressure lubricant consisting essentially of lubricating oil, about 10 to 60 wt. % of oil soluble compound of the formula:

$$Cl_3C-S-S-R$$

wherein R is an alkyl radical containing 8 to 30 carbon atoms, said compound tending to liberate HCl; and about 0.5 to 5% by weight, based on the weight of said extreme pressure compound, of an oil soluble basic stabilizer which acts as an acid trap by reacting with said HCl and inhibits liberation of halogen and sulphur from said extreme pressure compound at temperatures below 200° C., said stabilizer being selected from the group consisting of basic alkaline earth metal alkylbenzene sulphonates, basic alkaline earth metal phenates, epoxy resins, dicarboxylic acid esters, salts of fatty acid and heterocyclic nitrogen containing compounds, and mixtures thereof.

* * * * *